US010934581B2

(12) United States Patent
Royyuru

(10) Patent No.: US 10,934,581 B2
(45) Date of Patent: Mar. 2, 2021

(54) BOW TIE DNA COMPOSITIONS AND METHODS

(71) Applicant: International Business Machines Corporation, Armonk, NY (US)

(72) Inventor: Ajay K. Royyuru, Congers, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 308 days.

(21) Appl. No.: 16/051,722

(22) Filed: Aug. 1, 2018

(65) Prior Publication Data

US 2018/0334710 A1 Nov. 22, 2018

Related U.S. Application Data

(63) Continuation-in-part of application No. 14/580,532, filed on Dec. 23, 2014, now abandoned.

(60) Provisional application No. 61/986,343, filed on Apr. 30, 2014.

(51) Int. Cl.
| *C12Q 1/68* | (2018.01) |
| *C12Q 1/6869* | (2018.01) |
| *C12Q 1/6853* | (2018.01) |
| *B82Y 15/00* | (2011.01) |
| *C12N 15/10* | (2006.01) |
| *C12Q 1/6806* | (2018.01) |
| *B82Y 5/00* | (2011.01) |

(52) U.S. Cl.
CPC ............ *C12Q 1/6869* (2013.01); *B82Y 15/00* (2013.01); *C12N 15/10* (2013.01); *C12Q 1/6806* (2013.01); *C12Q 1/6853* (2013.01); *B82Y 5/00* (2013.01); *C12Q 2525/313* (2013.01)

(58) Field of Classification Search
None
See application file for complete search history.

(56) References Cited

U.S. PATENT DOCUMENTS

| 5,552,278 | A | 9/1996 | Brenner |
| 6,428,959 | B1 | 8/2002 | Deamer |
| 6,723,513 | B2 | 4/2004 | Lexow |
| 7,972,858 | B2 | 7/2011 | Meller et al. |
| 9,846,141 | B2 | 12/2017 | Royyuru |
| 9,846,142 | B2 | 12/2017 | Royyuru |
| 2009/0035777 | A1 | 2/2009 | Kokoris et al. |
| 2010/0240101 | A1 | 9/2010 | Lieberman et al. |
| 2010/0331194 | A1 | 12/2010 | Turner et al. |
| 2011/0005918 | A1 | 1/2011 | Akeson et al. |
| 2011/0214991 | A1 | 9/2011 | Kim et al. |
| 2011/0279125 | A1 | 11/2011 | Bedell et al. |
| 2011/0287414 | A1 | 11/2011 | Chen et al. |
| 2012/0010085 | A1 | 1/2012 | Rava et al. |
| 2014/0174929 | A1* | 6/2014 | Luan ................ G01N 27/447 204/543 |
| 2015/0315637 | A1 | 11/2015 | Royyuru |
| 2015/0315638 | A1 | 11/2015 | Royyuru |
| 2015/0316504 | A1 | 11/2015 | Royyuru |
| 2016/0077078 | A1 | 3/2016 | Huber et al. |
| 2016/0216233 | A1 | 7/2016 | Hovis et al. |
| 2016/0244823 | A1 | 8/2016 | Yoshida et al. |

OTHER PUBLICATIONS

List of IBM Patents or Patent Applications Treated as Related; YOR920120905US03, Date Filed: Aug. 1, 2018, 2 pages.
Butler, Tom Z. et al., "Determination of RNA Orientation during Translocation through a Biological Nanopore," Biophysical Journal, vol. 90, Jan. 2006, pp. 190-199.
Gadaleta et al., "Sub-additive ionic transport across arrays of solid-state nanoopres," Physics of Fluids 26, Jan. 2005 (2014).
Jun et al., "Rapid Fabrication of Uniformly Sized Nanopores and Nanopore Arrays for Parallel DNA Analysis", Advanced Materials, DOI: 10.1002/adma.200601191, 2006, vol. 18, pp. 3149-3153.
Mcnally, Ben et al., "Optical Recognition of Converted DNA Nucleotides for Single-Molecule DNA Sequencing Using Nanopore Arrays," Nano Lett., vol. 10, No. 6, 2010, pp. 2237-2244.
Meller Group, "Fabrication of Solid-state nonopores and nanopore arrays", Single Molecule Biophysics & Nano-biotechnology, BME, 2006, p. 1.
Raza et al., "Crosstalk between adjacent nanopores in a solid-state membrane array for multi-analyte high-throughput biomolecule detection," Journal for of Applied Physics 120, 064701 (2016).
Sauer-Budge, Alexis F. et al., "Unzipping Kinetics of Double-Stranded DNA in a Nanopore," Phys. Rev. Lett., vol. 90, No. 23, 2003, 238101, 4 pages.
Schmidt et al., "Nanopore arrays in a silicon membrane for parallel single-molecule detection: fabrication," Nanotechnology 26 (2015).
Seeman, Nadrian C. et al., "Two Dimensions and Two States in DNA Nanotechnology," Journal of Biomolecular Structure & Dynamics, Conversation 11, Issue 1, 2000, pp. 253-262.
Skinner, Gary M. et al., "Distinguishing Single- and Double-Stranded Nucleic Acid Molecules Using Solid-State Nanopores," Nano Lett., vol. 9, No. 8, 2009, pp. 2953-2960.
Stewart, Robert., "Deoxyribonucleic acid (DNA)", Virtual Cell Radiobiology Software Manual, downloaded Apr. 11, 2017, pp. 1-4.
Venta et al, Differentiation of Short, Single-Stranded DNA Homopolymers in Solid-State Nanopores, ACSNANO, vol. 7, No. 5, 2013, pp. 4629-4636.

(Continued)

*Primary Examiner* — James Martinell
(74) *Attorney, Agent, or Firm* — Cantor Colburn LLP; Kristofer Haggerty

(57) ABSTRACT

A bow tie DNA composition is three duplex DNA segments in a forked structure comprising a duplex stem, a duplex first fork and a duplex second fork, wherein a first strand of the stem and a first strand of the first fork form a first contiguous DNA strand, wherein a second strand of the stem and a first strand of the second fork form a second contiguous DNA strand, and wherein the first strand of the first fork and the first strand of the second fork are not complementary.

7 Claims, 3 Drawing Sheets
Specification includes a Sequence Listing.

(56) References Cited

OTHER PUBLICATIONS

Venta et al., "Supporting Information for Differentiation of Short Single-Stranded DNA Homopolymers in Solid-State Nanopores", ACSNANO, vol. 7, No. 5, 2013, pp. 4629-4636.
Wang, Hai-Jun et al., "Cooperative translocation dynamics of biopolymer chains through nanopores in a membrane: Slow dynamics limit," Eur. Phys. J. E, vol. 33, No. 3, Nov. 2010, pp. 251-258.
Wikipedia "Algae"; retrieved from Internet Mar. 4, 2016; https://en.wikipedia.org/wiki/Algae[Mar. 4, 2016 4:59:55 PM]; 20 pgs.
Wikipedia "Archaea" retrieved May 11, 2016; https://en.wikipedia.org/wiki/Archaea[May 11, 2016 8:03:51 PM]; 26 pgs.
Wikipedia "Fish"; retrieved Nov. 2, 2014; http://en.wikipedia.org/wiki/Fish; 11 pgs.
Wikipedia "Fungus"; retrieved Jun. 3, 2013; http://en.wikipedia.org/wiki/Fungi[Jun. 3, 2013 9:22:10 AM]; 28 pgs.
Wikipedia "Mammal", retrieved Sep. 22, 2011; http://en.wikipedia.org/wiki/Mammals; 17 pgs.
Wikipedia "Murinae", retrieved Mar. 18, 2013; http://en.wikipedia.org/wiki/Murinae[Mar. 18, 2013 3:50:51 PM]; 21 pgs.
Wikipedia "Plant", retrieved Aug. 28, 2015; https://en.wikipedia.org/wiki/Plant; 14 pgs.
Wikipedia "Protozoa", retrieved May 11, 2016; https://en/wikipedia.org/wiki/Protozoa[May 11, 2016 4:03:51 PM]; 10 pgs.
Wikipedia "Virus", retrived Nov. 24, 2012; http://en.wikipedia.org/wik/Virus; 34 pgs.
Wisegeek How Many Species of Bacteria Are There? retrieved Jan. 21, 2014; http://www.wisegeek.org/how-many-species-of-bacteria-are-there.htm; 2 pgs.

\* cited by examiner

BOW TIE DNA COMPOSITIONS AND METHODS

DOMESTIC PRIORITY

This application is a continuation-in-part of and claims priority to U.S. patent application Ser. No. 14/580,532, filed on Dec. 23, 2014, which claims priority to U.S. Provisional Application No. 61/986,343, filed Apr. 30, 2014, the entire contents of both applications are incorporated herein by reference in their entirety.

BACKGROUND

The present invention generally relates to nucleic acid structures and their methods of use, particularly in sequencing methods, and more specifically, to a bow tie DNA structure.

DNA sequencing is the determination of the order in which nucleotides occur on a strand of deoxyribonucleic acid (DNA). Special emphasis has been given, for example, to the application of nanopores for DNA sequencing, which has promise in reducing the cost of DNA sequencing. A nanopore is a small hole on the order of several nanometers in internal diameter. The theory behind nanopore sequencing has to do with what occurs when the nanopore is immersed in a conducting fluid and an electric potential (voltage) is applied across it: under these conditions a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. In order to facilitate DNA sequencing, the DNA must be captured by the nanopore device and single stranded DNA made available for sequencing.

SUMMARY

According to one embodiment, a bow tie DNA composition comprises three duplex DNA segments in a forked structure comprising a duplex stem, a duplex first fork and a duplex second fork, wherein a first strand of the stem and a first strand of the first fork form a first contiguous DNA strand, wherein a second strand of the stem and a first strand of the second fork form a second contiguous DNA strand, and wherein the first strand of the first fork and the first strand of the second fork are not complementary.

In another embodiment, a kit comprises two to four strands of DNA capable of forming a bow tie DNA structure, a DNA ligase, and a reaction buffer.

In yet another embodiment, a method of making a modified double-stranded target DNA comprises ligating a double-stranded target DNA to a bow tie DNA as described above to produce the modified double-stranded target DNA.

In yet another embodiment, a method for analyzing one or more double-stranded target DNAs comprises providing the double-stranded target DNAs ligated to a bow tie DNA, and contacting the ligated bow tie-DNA-target DNAs with a membrane containing at least one nanopore.

DETAILED DESCRIPTION

Figure 1:
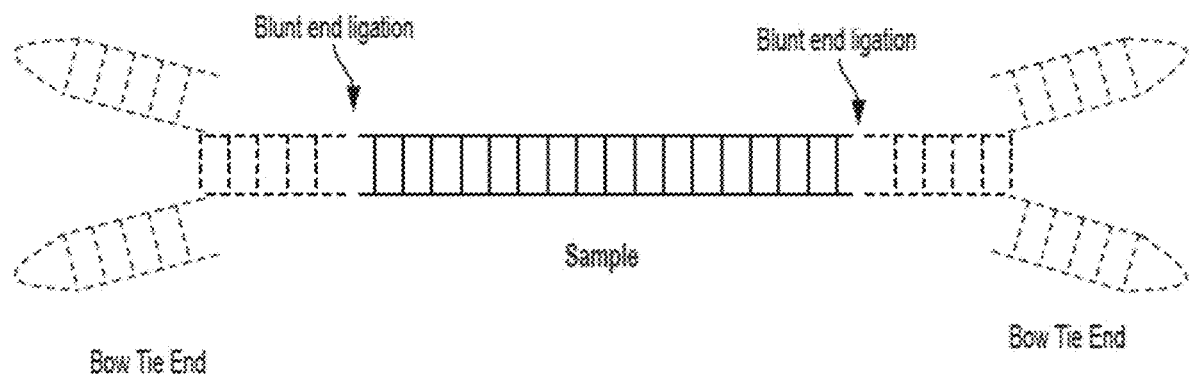
FIG. 1 shows an embodiment of a bow tie DNA molecule ligated onto both ends of a double-stranded target molecule from a sample.

The bow tie DNA molecules described herein are particularly well-suited for use in nanopore sequencing methods. When a nanopore is immersed in a conducting fluid and an electric potential (voltage) is applied across the nanopore, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore. One problem with nanopore sequencing is that double stranded DNA is stable and does not easily unwind to present separate strands. The bow tie DNA structures described herein can be ligated to double-stranded DNA samples providing modified targets that are well-suited for nanopore sequencing techniques. FIG. 1 illustrates a bow tie DNA ligated to a target DNA from a sample.

In one embodiment or more embodiments of the present invention, a bow tie DNA composition, comprises three duplex DNA segments in a forked structure comprising a duplex stem, a duplex first fork and a duplex second fork, wherein a first strand of the stem and a first strand of the first fork form a first contiguous DNA strand, wherein a second strand of the stem and a first strand of the second fork form a second contiguous DNA strand, and wherein the first strand of the first fork and the first strand of the second fork are not complementary.

Figure 2:
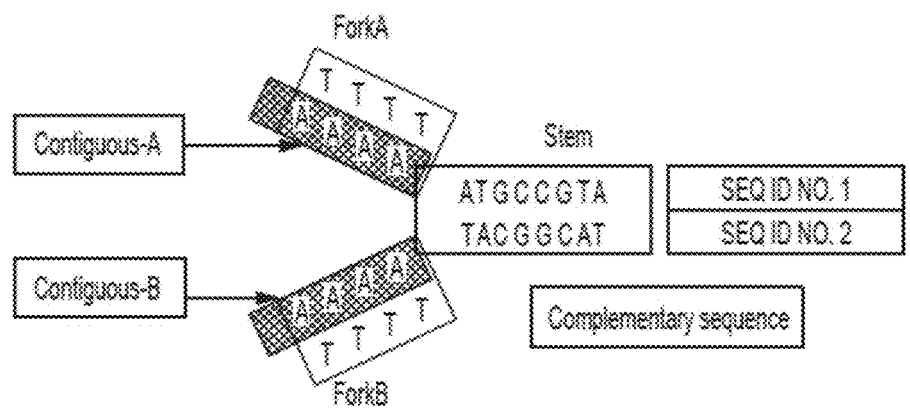
FIG. 2 is an embodiment of a bow tie DNA illustrating the contiguous sequence between the stem and the forks.
Figure 3:
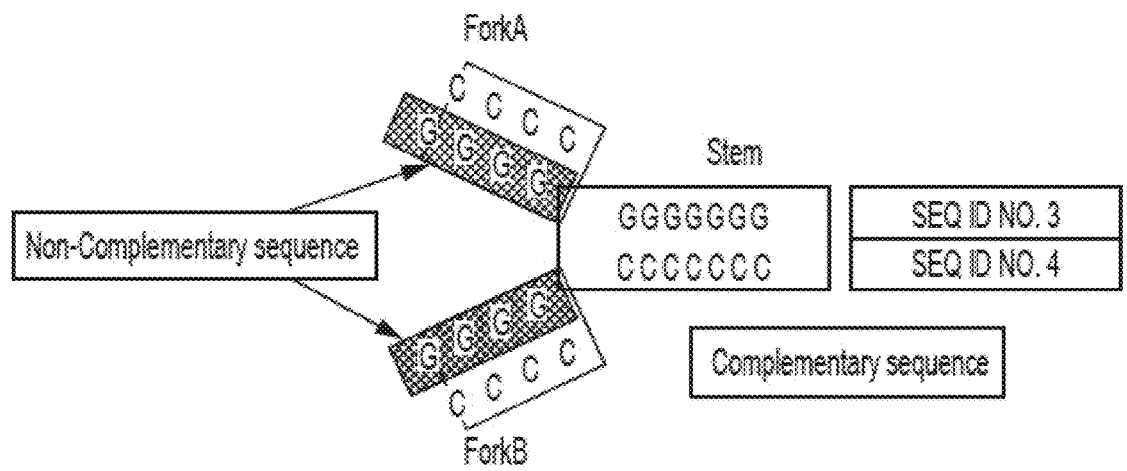
FIG. 3 is an embodiment of a bow tie DNA illustrating the non-complementary sequence in the forks.
Figure 4:
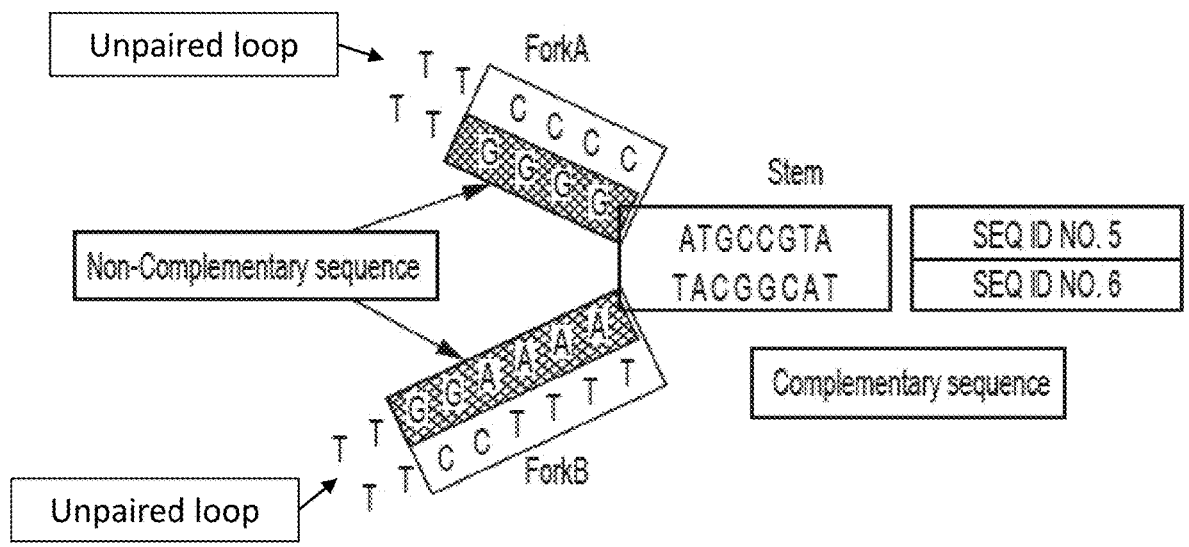
FIG. 4 is an embodiment of a bow tie DNA illustrating a two strand structure in which each strand contains a stem strand-first fork strand-loop-second fork strand, wherein the first and second fork strands are complementary.

FIGS. 2-4 illustrate embodiments of bow tie DNAs of the present disclosure. The sequences of the stem/fork strands in FIG. 2 are as follows:

5'ATGCCGTAAAAA3'     SEQ ID NO. 1

5'TACGGCATAAAA3'     SEQ ID NO. 2

The sequences of the stem/fork strands in FIG. 3 are as follows:

5'GGGGGGGGGGG3'     SEQ ID NO. 3

5'CCCCCCCCCCC3'     SEQ ID NO. 4

The sequences of the stem/fork strands in FIG. 4 are as follows:

```
                                              SEQ ID NO. 5
5'ATGCCGTAGGGGTTTTCCCC3'

SEQ ID NO. 6
5'TACGGCATTTTCCTTTGGAAAA5'
```

In FIGS. 2 and 3, the second strand of the first fork and the second strand of the second fork are not contiguous with the first and second strands of the stem. That is, the bow tie DNA comprises four strands of DNA. In FIG. 2, a first strand of the stem is contiguous with a first strand of the first fork, and a second strand of the stem is contiguous with a first strand of the second fork. In other words, the first strand of the stem and a first strand of the first fork form a single, contiguous polynucleotide chain. Similarly, the second strand of the stem and the first strand of the second fork form a single, contiguous polynucleotide chain. FIG. 3 illustrates that the first strand of the first fork and the first strand of the second fork are not complementary. In essence, because the first strand of the first fork and the first strand of the second fork are not complementary, they are free to bind their respective second strands, thus forming the double-stranded forked structure of the bow tie DNA.

FIG. 4 illustrates an alternative embodiment, wherein the bow tie DNA comprises two contiguous strand of DNA. The first contiguous strand of DNA comprises, in order, the first strand of the stem, the first strand of the first fork, a first unpaired loop, and the second strand of the first fork. The second contiguous strand of DNA comprises, in order, the second strand of the stem, the first strand of the second fork, a second unpaired loop, and the second strand of the second fork. In this embodiment, the first and second strands of the forks are joined by the unpaired loops. The unpaired loops include DNA bases that are not paired to other bases. According to the exemplary embodiments of the present invention shown in FIG. 4, the unpaired loops each have sequence of 5'TTTT3'. The unpaired loops, as shown, make the entire sequence of ForkA and the top strand of the stem a single DNA chain, as well as the entire sequence of ForkB and the bottom strand of the stem a single DNA chain. According to one or more embodiments of the present invention, each unpaired loop includes 4 to 6 base pairs.

Under normal operating conditions of pH, temperature and salt, the DNA strands will self-assemble to form the bow tie DNA structure. This secondary structure has the distinct property of presenting double stranded fork segments that have a tendency stay apart (splayed ends), due to the rigid structure of double stranded DNA and electrostatic repulsion of negative charges on phosphates of DNA backbone on adjacent fork segments. This electrostatic repulsion and splay will be pronounced at low salt concentration, due to reduced screening of negative charge on phosphate groups.

Bow tie DNA structures, including forks and stems, are selected to maintain a stable bow tie secondary structure. In one or more embodiments of the present invention, the lengths of the forks and the stem are chosen to provide the desired separation of the ends of the forks. In some embodiments of the present invention, the forks have lengths of 4 to 100 nucleotides; and in other embodiments of the present invention, the forks have lengths of 4 to 20 nucleotides. In one or more embodiments of the present invention; the stem has a length of 8 to 100 nucleotides; and in other embodiments of the present invention, the stem has a length of 8 to 25 nucleotides.

Figure 5:
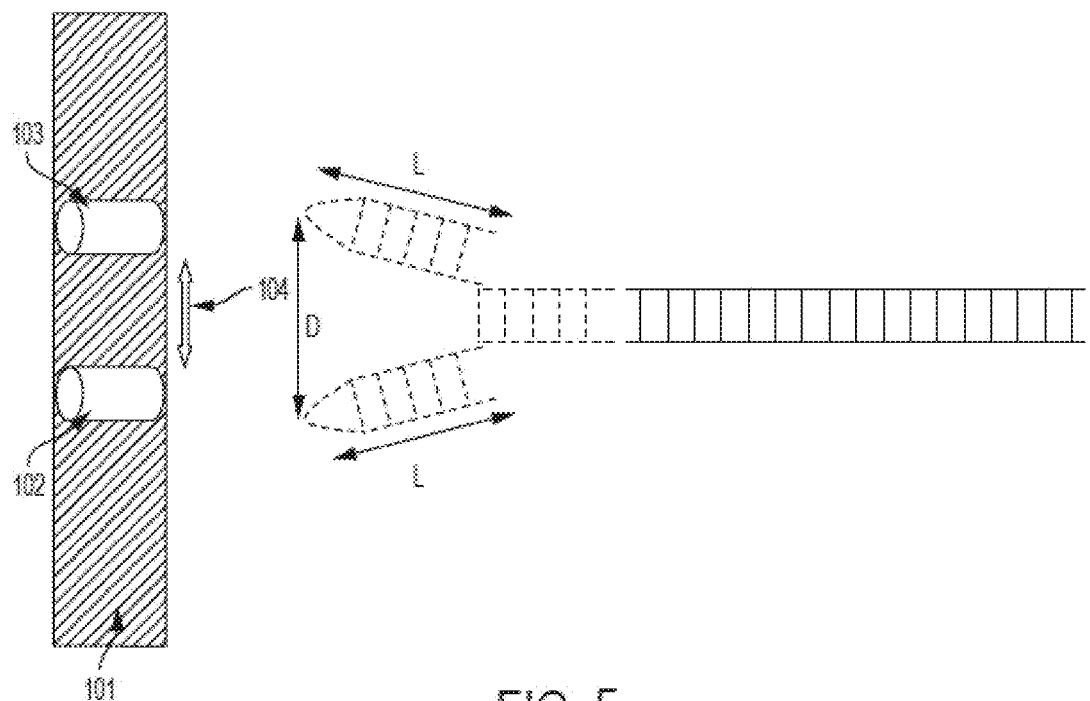
FIG. 5 illustrates the presentation of a bow tie DNA-double stranded target DNA ligation product presented to a pair of nanopores in a membrane.

The length of ForkA and ForkB can be increased or decreased by adding or removing nucleotides of complementary sequence to the double stranded stretch of the forks (L). This will manifest as greater or lesser physical distance between the ends of the forks (D). (FIG. 5)

Further, bow tie DNAs can be readily designed by one of ordinary skill in the art using the common knowledge of DNA hybridization and the calculation of melting temperatures for DNA duplexes. The $T_m$ of any nucleic acid duplex can be directly measured, using techniques well known in the art. For example, a thermal denaturation curve can be obtained for the duplex, the midpoint of which corresponds to the $T_m$. The $T_m$ for a particular duplex (e.g., an approximate $T_m$) can also be calculated. For example, the $T_m$ for an oligonucleotide-target duplex can be estimated using the following algorithm, which incorporates nearest neighbor thermodynamic parameters: $T_m(Kelvin)=\Delta H°/(\Delta S°+R \ln C_t)$, where the changes in standard enthalpy ($\Delta H°$) and entropy ($\Delta S°$) are calculated from nearest neighbor thermodynamic parameters, R is the ideal gas constant (1.987 cal·K$^{-1}$ mole$^{-1}$), and $C_t$ is the molar concentration of the oligonucleotide. The calculated $T_m$ is optionally corrected for salt concentration, e.g., Na$^+$ concentration, using the formula:

$$1/T_m(Na^+)=1/T_m(1M)+(4.29f(G·C)-3.95)\times10^{-5} \ln [Na^+]+9.40\times10^{-6} \ln^2[Na^+].$$

In one embodiment, the stem comprises a blunt end opposite the forks which is suitable for blunt-ended ligation to a target DNA sequence.

The bow tie DNA structures as described herein are particularly well-suited for ligation to a double-stranded target DNA molecule which is then subjected to an analysis, such as sequencing using a nanopore. Ligation can be blunt end ligation or ligation to a double-stranded target DNA that has a single-stranded overhang.

In one embodiment, blunt-ended ligation of the bow tie DNA to a double-stranded target DNA is performed in a molar excess of the bow tie DNA, such as a 2-fold, 10-fold, or greater molar excess of the bow tie DNA. While the use of a molar excess of bow tie DNA is expected to produce an increased number of bow-tie-bow tie conjugates, it should reduce the number of target DNA molecules that are ligated to each other without also being ligated to at least one bow tie DNA. Thus, the expected products of blunt ended ligation are bow-tie-bow-tie conjugates, bow-tie-target conjugates containing one or more target molecules, and a small number of target-target conjugates. When the ligated products are analyzed, for example, by nanopore sequencing, the short bow-tie-bow-tie complexes have known sequences and will be readily recognized. More importantly, the target strands with ligated bow tie DNA will be readily recognized by the known sequence of the bow-tie DNA.

In a further embodiment, a kit comprises two to four strands of DNA capable of forming a bow tie DNA structure, DNA ligase, and a reaction buffer. The kit optionally further comprises instructions for assembling the bow tie DNA and ligating the bow tie DNA to a target DNA. Reaction buffers are well-known in the art and include buffers and salts at suitable concentrations to perform a DNA ligation.

In one embodiment, a method for analyzing one or more double-stranded target DNAs comprises providing the double-stranded target DNAs ligated to a bow tie DNA, and contacting the ligated bow tie-DNA-target DNAs with a membrane containing at least one nanopore. In one embodiment, analyzing comprises sequencing at least one strand of the double-stranded target DNA.

The modified target DNAs ligated to a bow tie DNA are useful for nanopore sequencing, particularly nanopore sequencing using a modified nanopore device comprising one or more pairs of nanopores, wherein the distance between the two nanopores of the pair is equal to the distance between the two forks of the bow tie DNA. Such a device is illustrated in FIG. 5.

According to one or more embodiments of the present invention, each nanopore (nanopore one (102) and nanopore two (103)) has a diameter of 2 nm to 50 nm. A minimum diameter of 2 nm allows the passage of double stranded DNA of the two forks (ForkA and ForkB as shown in FIGS. 2-4) of the bow tie DNA. A maximum diameter of 50 nm achieves separate passage of each fork of the bow tie DNA (ForkA and ForkB) through respective nanopores (nanopore one (102) and nanopore two (103)).

The distance (104) between nanopore one (102) and nanopore two (103) in the membrane (101) is equal to the distance (D) between the two forks of the bow tie DNA. Without being held to theory, it is believed that by matching distance 104 between the nanopores to distance D in the bow tie DNA, the two forks of the bow tie DNA will each thread through one of the matched nanopores. In this way, the DNA, as it moves through the nanopores, will unwind as it translocates from the source side of the membrane 101 to the sink side of the membrane. That is, one single strand of the modified target DNA will thread through each nanopore of the pair. Further, once the single strands pass to the sink side of the membrane, the energetics of hybridization will drive the single strands to helical rewinding. In this way, while the DNA in physical proximity to the pores 102 and 103 is single-stranded, the DNA above and below the membrane 101 will be double-stranded, leading to a "stretched" configuration within the membrane 101. This stretched configuration will allow for maximal spatial separation of the DNA bases of the single-stranded DNA, increasing the fidelity and resolution of sequencing. Thus, the ligation of bow tie DNA to a double-stranded target DNA provides a novel presentation of double-stranded DNA to a nanopore device comprising pairs of nanopores which should eliminate the DNA preparation steps of fragmentation and unwinding.

Figure 6:
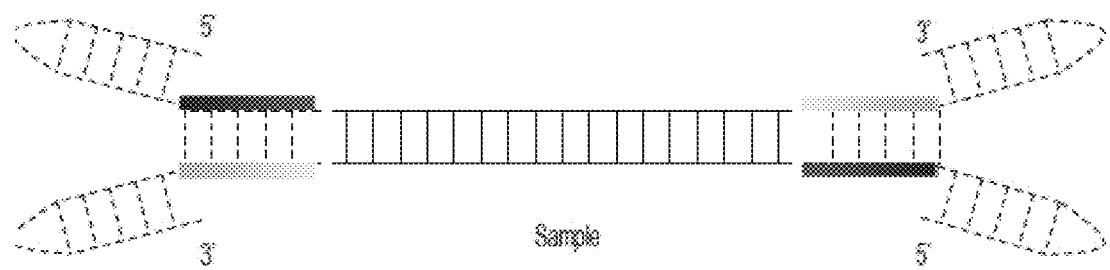
FIG. 6 is a schematic showing the ligation of fixed bow tie DNA sequences to a blunt-ended double-stranded target DNA. The known sequence and polarity (5', 3') of the bow tie DNA sequence can be used to identify the ends of the target DNA and to determine the strand direction of the target DNA.

Another advantage of the use of bow tie DNAs as described herein is a result of the fixed or known sequence of the bow tie DNA. One problem with sequencing in a nanopore is not being able to determine the strand direction, that is, 5→3' or 3→5'. As illustrated in FIG. 6, reading the sequence of the bow tie ends allows identification of the strand direction as the DNA passes through the channel. As shown in FIG. 6, sequencing the header or tail of bow tie DNA in each strand will allow for identification of strand direction. Known methods of computational biology can then be used to identify the strand of DNA sequenced within the human genome, for example.

According to one or more embodiments of the present invention, the target DNA from the sample (e.g., as shown in FIG. 1 and FIG. 6) to be sequenced includes sample lengths of 1 base pair to 10 million base pairs (Mbps). The limiting factor in terms of length of target DNA from the sample to be sequenced is the instability of long, naked DNA strands. Yet, operating the device at lower temperatures, e.g., −4° C. to −80° C., can increase the stability.

According to some embodiments of the present invention, the stem region of the bow tie DNA is sufficient by itself to hybridize outside the nanopores, separate into single strands for passage through the pores, and re-hybridize after passage through the pores, and therefore, in some embodiments, therefore, the target DNA to be sequenced includes 0 base pairs.

As used herein, polynucleotides include DNA and RNA, and are polymeric, contiguous, i.e., covalently bonded, strands of nucleotides.

"Complementary" or "substantially complementary" refers to the hybridization or base pairing or the formation of a duplex between nucleotides or nucleic acids, such as, for instance, between the two strands of a double-stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more specifically about 98 to 100%. Alternatively, substantial complementarity exists when an RNA or DNA strand will hybridize under selective hybridization conditions to its complement. Typically, selective hybridization will occur when there is at least 65% complementary over a stretch of at least 14 to 25 nucleotides, specifically at least about 75%, more specifically at least about 90% complementary.

The term "single stranded DNA" (ssDNA) as used herein refers to a naturally occurring or synthetic deoxyribonucleic acid molecule comprising a linear single strand, for example, a ssDNA can be a sense or antisense gene sequence.

"Duplex" is used interchangeably with "double-stranded" and means at least two oligonucleotides and/or polynucleotides that are fully or partially complementary and that undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g., conditions including temperature of about 5° C. less that the $T_m$ (melting temperature) of a strand of the duplex and low monovalent salt concentration, e.g., less than 0.2 M, or less than 0.1 M. "Perfectly matched" in reference to a duplex means that the poly- or oligonucleotide strands making up the duplex from a double Watson-Crick basepairing with a nucleotide in the other strand. The term "duplex" includes the pairing of nucleoside analogs, such as deoxyinosine, nucleosides with 2-aminopurine bases, PNAs, and the like, that may be employed. A "mismatch" in a duplex between two oligonucleotides or polynucleotides means that at pair of nucleotides in the duplex fails to undergo Watson-Crick bonding.

"Hybridization" refers to the process in which two single-stranded polynucleotides bind non-covalently to form a stable double-stranded or duplex polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM or less than about 200 mM. Hybridization temperatures can be as low as 5° C., but are typically greater than 22° C., more typically greater than about 30° C., and specifically in excess of about 37° C.

Hybridizations are usually performed under stringent conditions, i.e., conditions under which a probe will specifically hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at a defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 5.0 mM sodium phosphate, 5 mM EDTA, pH 7.4) and a temperature of 25-30° C. are suitable for allele-specific probe hybridizations. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

The term "blunt end" as used herein refers to the end of a dsDNA molecule having 5' and 3' ends, wherein the 5' and 3' ends terminate at the same nucleotide position. Thus, the blunt end comprises no 5' or 3' overhang.

"Ligation" means to form a covalent bond or linkage between the termini of two or more nucleic acids, e.g. oligonucleotide and/or polynucleotide. Ligation included blunt-end ligation as well as ligation with a single strand overhang. The nature of the bond or linkage may vary widely and the ligation may be carried out enzymatically or chemically. In one embodiment, ligations are carried out enzymatically to form a phosphodiester linkage between a 5' carbon of a terminal nucleotide of one oligonucleotide with 3' carbon of another oligonucleotide. Examples of ligases include Taq DNA ligase, T4 DNA ligase, T7 DNA ligase, and E. coli DNA ligase. The choice of the ligase depends to a certain degree on the design of the ends to be joined together. Thus, if the ends are blunt, T4 DNA ligase may be employed, while a Taq DNA ligase may be preferred for a sticky end ligation, i.e. a ligation in which an overhang on each end is a complement to each other.

As used herein, a "target polynucleotide" or "target DNA" is a polynucleotide from a sample. In one embodiment, a target polynucleotide is a double stranded polynucleotide (e.g., DNA) for which the nucleotide sequence is to be determined. A target polynucleotide, following extraction from a sample, is processed such that the target polynucleotide has a length of 1 base pair to 10 million base pairs (Mbps). Despite the source of the sample, the target polynucleotide includes the following bases (G, A, T, and C).

A sample may be collected from an organism, mineral or geological site (e.g., soil, rock, mineral deposit, combat theater), forensic site (e.g., crime scene, contraband or suspected contraband), or a paleontological or archeological site (e.g., fossil, or bone) for example. A sample may be a "biological sample," which refers to a material obtained from a living source or formerly-living source, for example, an animal such as a human or other mammal, a plant, a bacterium, a fungus, a protist or a virus. The biological sample can be a solid material such as a tissue, cells, a cell pellet, a cell extract, or a biopsy, or a biological fluid such as urine, blood including plasma or serum, saliva, amniotic fluid, exudate from a region of infection or inflammation, or a mouth wash containing buccal cells, urine, cerebral spinal fluid and synovial fluid and organs.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for analyzing a double-stranded target DNA molecule, comprising:

providing the double-stranded target DNA molecule ligated to a bow tie DNA, the double-stranded target DNA molecule having 1 base pair to 10 million base pairs, and the bow tie DNA comprising:

a first contiguous DNA strand and a second contiguous DNA strand, the bow tie DNA further comprising:

three duplex DNA segments in a forked structure comprising a duplex stem comprising a stem top strand and a stem bottom strand, a duplex first fork comprising a first fork top strand and a first fork bottom strand, and a duplex second fork comprising a second fork top strand and a second fork bottom strand, wherein a stem top strand and a first fork bottom strand form the first contiguous DNA strand, wherein a stem bottom strand and a second fork top strand form the second contiguous DNA strand, and wherein the first fork bottom strand and the second fork top strand are not complementary;

contacting the ligated bow tie-DNA-target DNA molecule with a membrane comprising a pair of nanopores, each nanopore of the pair of nanopores having a diameter of 2 to 50 nanometers (nm);

applying an electric potential to the membrane comprising the pair of nanopores;

passing the ligated bow tie-DNA-target DNA molecule through the pair of nanopores, the double stranded target DNA unwinding into a first single DNA strand and a second single DNA strand such that the first single DNA strand translates through a first nanopore of the pair of nanopores, and the second single DNA strand translates through the second nanopore of the pair of nanopores; and sequencing the double stranded target DNA molecule, based on a change in magnitude of a current in the pair of nanopores.

2. The method of claim 1, wherein analyzing comprises sequencing at least one strand of the double-stranded target DNA.

3. The method of claim 1, wherein a distance between the first nanopore and the second nanopore is equal to the distance between the forks of the bow tie DNA.

4. The method of claim 1, wherein, in the bow tie DNA, a second strand of the first fork is not contiguous with the first contiguous DNA strand, and wherein a second strand of the second fork is not contiguous with the second contiguous DNA strand.

5. The method of claim 1, wherein, in the bow tie DNA, the first contiguous DNA comprises, in order, the first strand of the stem, the first strand of the first fork, a first unpaired loop, and a second strand of the first fork, and the second contiguous DNA strand comprises, in order, the second strand of the stem, the first strand of the second fork, a second unpaired loop, and a second strand of the second fork.

6. The method of claim 1, wherein, in the bow tie DNA, the stem has a blunt end opposite the forks.

7. The method of claim 1, wherein, the sequence of one or more strands of the stem, the first fork, or the second fork is used to determine the 5'-3' or 3'-5' orientation of a strand of the target DNA as it passes through the nanopore.

* * * * *

SEQUENCE LISTING

<160> NUMBER OF SEQ ID NOS: 6

<210> SEQ ID NO 1
<211> LENGTH: 12
<212> TYPE: DNA
<213> ORGANISM: Artificial Sequence
<220> FEATURE:
<223> OTHER INFORMATION: bow tie DNA strand

<400> SEQUENCE: 1
atgccgtaaa aa                                                          12

-continued

```
<210> SEQ ID NO 2
<211> LENGTH: 12
<212> TYPE: DNA
<213> ORGANISM: Artificial Sequence
<220> FEATURE:
<223> OTHER INFORMATION: bow tie DNA strand

<400> SEQUENCE: 2
tacggcataa aa                                                         12

<210> SEQ ID NO 3
<211> LENGTH: 11
<212> TYPE: DNA
<213> ORGANISM: Artificial Sequence
<220> FEATURE:
<223> OTHER INFORMATION: bow tie DNA strand

<400> SEQUENCE: 3
gggggggggg g                                                          11

<210> SEQ ID NO 4
<211> LENGTH: 11
<212> TYPE: DNA
<213> ORGANISM: Artificial Sequence
<220> FEATURE:
<223> OTHER INFORMATION: bow tie DNA strand

<400> SEQUENCE: 4
cccccccccc c                                                          11

<210> SEQ ID NO 5
<211> LENGTH: 20
<212> TYPE: DNA
<213> ORGANISM: Artificial Sequence
<220> FEATURE:
<223> OTHER INFORMATION: bow tie DNA strand

<400> SEQUENCE: 5
atgccgtagg ggttttcccc                                                 20

<210> SEQ ID NO 6
<211> LENGTH: 23
<212> TYPE: DNA
<213> ORGANISM: Artificial Sequence
<220> FEATURE:
<223> OTHER INFORMATION: bow tie DNA strand

<400> SEQUENCE: 6
tacggcattt ttcctttgga aaa                                             23
```